United States Patent [19]  [11] 4,218,563
Love et al.  [45] Aug. 19, 1980

[54] PROCESS FOR THE PREPARATION OF CEPHAMYCIN ANTIBIOTICS

[75] Inventors: George M. Love, Mountainside; Paul Sohar, Warren; Leonard M. Weinstock, Belle Mead, all of N.J.

[73] Assignee: Merck & Co., Inc., Rahway, N.J.

[21] Appl. No.: 25,293

[22] Filed: Mar. 30, 1979

[51] Int. Cl.$^2$ ............................................. C07D 501/06
[52] U.S. Cl. ...................................... 544/21; 424/246
[58] Field of Search ........................................... 544/21

[56] References Cited
U.S. PATENT DOCUMENTS 4,014,873   3/1977   Christensen et al. ................. 424/246
4,053,286   10/1977   Weinstock ............................... 544/21

Primary Examiner—Nicholas S. Rizzo
Attorney, Agent, or Firm—Hesna J. Pfeiffer; Julian S. Levitt

[57] ABSTRACT

An improved process for preparing the antibiotic compound 7β-(2-thienylacetamido)-7-methoxy-3-carbamoyloxymethyl-3-cephem-4-carboxylic acid, from the N-blocked esters of the compound 7β-(D-5-amino-5-carboxyvaleramido)-3-carbamoyloxymethyl-7-methoxy-3-cephem-4-carboxylic acid (Cephamycin C), by conducting the transacylation of the latter in a homogenous solution containing N-trimethylsilyl loweralkyl carbamates.

4 Claims, No Drawings

PROCESS FOR THE PREPARATION OF CEPHAMYCIN ANTIBIOTICS

RELATIONSHIP TO THE PRIOR ART

The first disclosure in the patent literature of transacylation of Cephamycin C is in U.S. Pat. No. 4,014,873, issued Mar. 29, 1977. This process was conducted in the presence of a silylating agent. An improved transacylation, utilizing molecular sieves is claimed in U.S. Pat. No. 4,053,286, issued Oct. 11, 1977. The general chemistry of the transacylation reaction is in Weinstock et al., "The Chemistry of Cephamycins IV. Acylation of Amides in the Presence of Neutral Acid Scavengers", *Tet. Letters*, 46, 3979 (1975).

The patent, U.S. Pat. No. 4,014,873, discloses silyl urethane reagents identical to those of the instant application, that is

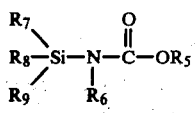

(Formula H, Col. 3) wherein $R_5$, $R_7$, $R_8$ and $R_9$ could be alkyl 1–8, and $R_6$ was hydrogen. A particular silyl urethane named included N-(trimethylsilyl)ethyl carbamate, also called N-trimethylsilyl ethyl urethane, Col. 9, line 17, and N-trimethylsilyl methyl urethane, Col. 9, lines 17–18.

The process disclosed in that patent was primarily directed to an acylation, e.g., with thienylacetyl chloride of Cephamycin C, the latter being a fermentation product prepared from *Streptomyces lactamdurans* NRRL 3802, on permanent unrestricted deposit. Under certain conditions, (such as prolonging the reaction time, Col. 9, line 38), this acylation was taught to proceed in one step, see Col. 9, lines 35 to Col. 10, line 7. None of the examples actually used the silyl urethanes of the above formula. When the silylating agent was used in the reaction, a molecular excess was employed, see Col. 38, lines 44–45, in claim 1.

SUMMARY OF THE INVENTION

It has now been discovered that using about an equivalent amount of a silyl urethane in the acylation reaction, a significantly higher, unexpected yield of final product can be quickly and easily recovered.

The silyl urethane of this invention is a trimethyl silyl loweralkyl carbamate,

where R is 1–4 carbon atoms, such as methyl, ethyl, or n-butyl. Particularly preferred is trimethylsilyl methyl carbamate.

The crux of this invention is the recognition that from about 0.8 to about 1.5 equivalents of the trimethylsilyl methyl carbamate, relative to Cephamycin C starting material is the optimal level to produce the final product in high yield. Generally, the reaction is conducted at about 80°–90° C., preferably 85° C., so that the internal pressure of reaction is about 30–45 psig., preferably about 40 psig. The reaction progress is monitered by liquid chromatographic assay of the amount of imide, or Cephamycin C having an thienylacetyl side chain at the 7-amino group in addition to its normal adipoyl group. When the imide level is at 2–5% the reaction is essentially complete (the theoretical level of 0% is probably reached, but is difficult to measure accurately); the reaction is then cooled quickly to from about 85° C. to about −10° C., in order to quench. The final product is then recovered. Generally, this reaction takes place in from 2–10 hours.

Although this reaction is best illustrated in the reaction of thienylacetyl chloride with Cephamycin C, a more generalized scheme is possible. Any acyl group of a 7-acylamido cephalosporin can be exchanged for another. The groups and definitions of breadth of this reaction are all those of U.S. Pat. No. 4,014,873, the contents of which are incorporated by reference.

A preferred embodiment is illustrated in the following flow sheet.

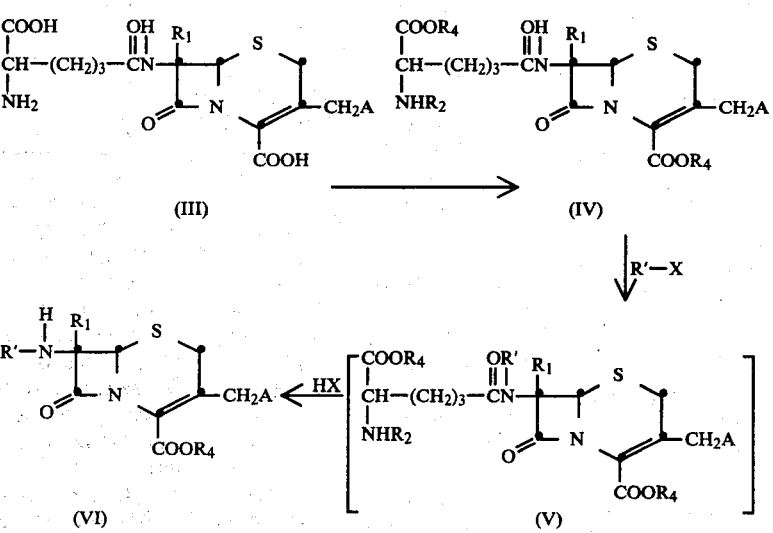

In the formulas of the above flowsheet, $R_1$ represents hydrogen or methoxy; A is as defined above, most desirably, acetoxy or carbamoyloxy; R′ represents an acyl group as defined above; $R_4$ represents hydrogen or a blocking or protecting substituent; and $R_2$ represents hydrogen or an amino blocking or protecting substituent.

The side chain amino protecting group, $R_2$, in compound (V) does not have to be easily removable since the side chain is removed in the transacylation process. In fact, it is preferred that the side chain amino protecting group be one that is not easily removed since these are usually less expensive and more stable to handling during manufacturing.

In accordance with this process, the amino group of the starting cephalosporin compound (III) is first blocked ($R_2$) by reaction with a suitable reagent to protect the 5'-amino-substituent of the aminoadipoyl side chain. Thus, the amino group is blocked by amino protecting groups such as acyl, aroyl, alkoxycarbonyl, alkylsulfonyl, arylsufonyl, and the like in accordance with methods well known in this art. Specific groups suitable for blocking the amino group that might be mentioned are those wherein $R_2$ is trichloroethoxycarbonyl, tertiary butoxycarbonyl, benzoylmethoxycarbonyl, trimethylsilyl, p-methoxybenzyloxy, 2-nitrophenylsulfenyl, 2,4-dinitrophenylsulfenyl, chloroacetyl, p-nitrophenylthio, p-nitrobenzensulfonyl, p-toluenesulfonyl, methanesulfonyl, benzoyl, p-chlorobenzoyl, p-nitrobenzoyl, toluoyl, and the like, although we generally prefer to utilize the p-toluenesulfonyl or benzoyl derivative which is conveniently prepared by reacting the cephalosporin compound with p-toluenesulfonyl chloride of benzoyl chloride while keeping the pH of the mixture basic, i.e., between 9 and 10.

It is generally preferred to carry out the above-described reactions with a cephalosporin compound, (IV), wherein the carboxy groups on the aminoadipoyl side chain, and at the 4-position are likewise blocked or protected since maximum yields of the desired product are obtained with such derivatives. Although the carboxy group on the aminoadipoyl side chain is not necessarily deblocked, since it is removed in the cleavage step, the blocking or protecting group $R_4$ at the 4-position is preferably one which can be removed easily to obtain the free acid without disruption of the $\beta$-lactam group since the cephalosporin compounds are usually used in the form of salts such as alkali metal salts or an amine salt. Protecting groups suitable for this purpose are well known in this art. The methoxymethyl group is particularly preferred. In a preferred embodiment of this invention, the methoxymethyl group is cleaved by mixing the products with excess water.

The protected cephalosporin compound is then reacted with an acylating agent, R'-X, in a homogenous solution in the presence of the trimethylsilyl methyl carbamate described above to obtain the diaylimide product (V). The acylating agent can be an acid halide (chloride or bromide), a functional equivalent thereof such as an acid anhydride, a mercaptide, a mixed acid anhydride with other carboxlic acids, an activated ester of the carboxylic acid such as the p-nitrophenyl ester, and the like. Thienylacetyl chloride is preferred.

The acylating agent is employed in amounts in molecular excess of that of the starting cephalosporin, preferably from 1 to 6 times as much acylating agent as cephalosporin, preferably in the range of 1 to 4 molar excess or most preferably in the range of 2 to 4 molar excess.

The silyl urethane is used in an amount approximately equivalent to the starting cephalosporin IV, or from 0.8 to 1.5 equivalents.

The acylation reaction takes place in a suitable solvent medium. The temperature at which this reaction is carried out is preferred to be from about 50° C. to 90° C. Various solvents which do not contain an active hydrogen such as chloroform, acetonitrile, methylene chloride, dioxane, benzene, halobenzene, carbon tetrachloride, 1,2-dichloroethane, and diethylether are most suitable as medium for the reaction mixture. The preferred solvent is methylene chloride. If desired, the reaction mixture is kept in motion by stirring or agitating during the reaction.

The cleavage to final product VI, under the conditions of solvent, temperature, amount of trimethylsilyl methyl carbamate, takes place spontaneously, due to liberation of acid from the reaction mixture products. The progress of reaction is monitored by decreased amounts of imide V, using standard liquid chromatographic or UV techniques. Generally, the reaction is completed within 2–10 hours, as evidenced by a drop in imide level to less than 5%.

This invention is illustrated by the following examples.

EXAMPLE 1

500 ml of a methylene chloride concentrate (dried to a Karl Fischer analysis of 0.08 g) of dimethoxymethyl ester of 7$\beta$-(D-5-tosylamino-5-carboxylvaleramido)-3-carbamoyloxymethyl-7-methoxy-3-cephem-4-carboxylic acid (54.4 mmoles) 13 ml (12 g, 81.6 mmoles, if pure) of trimethylsilyl methyl carbamate, and 27.2 ml (34.9 g, 217 mmoles, 4 eq.) of thienylacetyl chloride were sequentially charged to a 1 l. stirred autoclave and heated to 85° C. to afford an internal pressure of 40 psig. Samples were withdrawn at hourly intervals and assayed by lc.

| Hour | Sym Imide | Thienyl Product MM | Unsym. Imide | Thienyl Product Anhy |
|---|---|---|---|---|
| | | lc mole % | | |
| 1 | 11 | 48 | 18 | — |
| 2 | 14 | 61 | 8 | 1 |
| 3 | 9 | 73 | 4 | 2 |
| 4 | 3 | 76 | — | 3 |

| Hour | Starting Material MM | Mass Bal. | Total Imide |
|---|---|---|---|
| 1 | 31 | 108 | 29 |
| 2 | 16 | 100 | 22 |
| 3 | 12 | 100 | 11 |
| 4 | 9 | 91 | 3 |

The batch was quickly cooled at exactly 4.0 hours since this appeared to be the zero imide point. After cooling to 20° C., 447 g. (35.0 mmoles) of the batch was transferred from the autoclave to a 2 l. three neck flask with an overhead stirrer and cooled to −10° C. Seventy ml of ethanol was added and the mixture was aged for 30 minutes followed by the addition of 700 ml of room temperature water. The pH of the two phase mixture was adjusted to 5.0 with 1 NNaOH solution, and the methylene chloride was removed under reduced pressure.

The two phase mixture was vigorously stirred overnight at 22° C. while the pH was held at 5.0 by a pH meter switched pump which added 1 NNaOH solution as necessary to hold this pH. The crude mixture was then sequentially extracted 3 times at pH's of 4.4, 3.8 and 3.5 with 350 ml of methylene chloride. Lc assay of the 980 ml aqueous layer after the third extraction, column feed, was 12.1 g indicating a yield of 79%, as the carboxylic acid.

Isolation

After standing overnight at 6° C., the assay of the column feed had fallen from 12.1 g/l to 11.8 g/l. The column feed was then isolated using an IRA-68 chloride cycle resin column, followed by concentration using an XAD-2 resin column which was eluted with ethyl acetate. A breakthrough of 2.8% occurred on the IRA-68 column. Disregarding this breakthrough, the yield to ethyl acetate rich cut was 94%, and the overall yield to final product free acid hydrate was 85% with 2.5% in the mother liquors. Final product assays are given below.

| | |
|---|---|
| 1 c uncorrected purity, | 92.0% |
| EtOAc | 0.51% |
| HoAc | 0.53% |
| EtOH | 0.005% |
| KF | 4.30% |

EXAMPLE 2

The advantage of using from 1 to 1.5 equivalents of the trimethylsilyl methyl carbamate is illustrated by comparing total imide levels at various times in hours for differing concentrations of the carbamate:

| | Mole % of Total Imide by 1c | | | | |
|---|---|---|---|---|---|
| Equiv. | 1 hour | 2 hours | 3 hours | 4 hours | 5 hours |
| 1.5 | 35 | 30 | 15 | 0 | — |
| 2.3 | 60 | 57 | 40 | 24 | 4 |
| 3.0 | 72 | 65 | 49 | 30 | 15 |

(These figures were obtained by graphing observed points on a chart and reading extrapolations.)

The high amounts of imide indicate the reaction proceeds more slowly, with consequent economic disadvantage. Since the peak total imide level is dependent on trimethylsilyl methyl carbamate charge, the level of 1 to 1.5 equivalents accommodates various problems with purity of starting material or traces of water while not affording overlong reaction times.

Having fully described this invention, what is claimed is:

1. In the process of preparing the compound

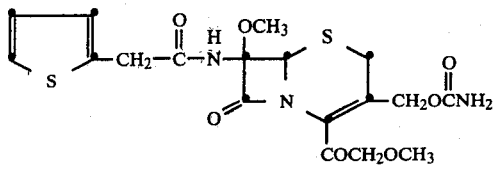

by reacting thienylacetyl chloride with

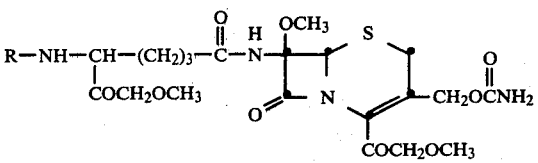

wherein R is p-tosyl in an inert solvent such as methylene chloride at a temperature of between 50°–90° C., the improvement comprising carrying out the reaction in the presence of about 0.8 to 1.5 equivalents of trimethylsilyl loweralkyl carbamate for a time sufficient to reduce the intermediate imide level to less than 5%, then quenching by cooling to between 20° C. and −10° C., and recovering the product thereby produced.

2. The process of claim 1 in which the trimethylsilyl loweralkyl carbamate has 1–4 carbon atoms in the loweralkyl.

3. The process of claim 1 in which trimethylsilyl methyl carbamate is used.

4. The process of claim 1 in which trimethylsilyl ethyl carbamate is used.

* * * * *